(12) United States Patent
Namkoong et al.

(10) Patent No.: US 12,419,863 B2
(45) Date of Patent: Sep. 23, 2025

(54) PHARMACEUTICAL COMPOSITION FOR USE IN TREATMENT OF HYPERTROPHIC CARDIOMYOPATHY

(71) Applicant: CELLTRION INC., Incheon (KR)

(72) Inventors: Hoon Namkoong, Incheon (KR); Bon Joong Kim, Incheon (KR); Bo Ram Lee, Incheon (KR); Eun Sun Choi, Incheon (KR)

(73) Assignee: CELLTRION INC., Incheon (KR)

( * ) Notice: Subject to any disclaimer, the term of this patent is extended or adjusted under 35 U.S.C. 154(b) by 970 days.

(21) Appl. No.: 17/288,610

(22) PCT Filed: Nov. 1, 2019

(86) PCT No.: PCT/KR2019/014726
§ 371 (c)(1),
(2) Date: Apr. 26, 2021

(87) PCT Pub. No.: WO2020/091512
PCT Pub. Date: May 7, 2020

(65) Prior Publication Data
US 2021/0393592 A1 Dec. 23, 2021

(30) Foreign Application Priority Data
Nov. 2, 2018 (KR) .................. 10-2018-0133958

(51) Int. Cl.
*A61K 31/4164* (2006.01)
*A61K 45/06* (2006.01)
*A61P 9/00* (2006.01)
*C07D 233/06* (2006.01)

(52) U.S. Cl.
CPC .......... *A61K 31/4164* (2013.01); *A61K 45/06* (2013.01)

(58) Field of Classification Search
CPC ....... A61K 45/06; A61K 31/4164; A61P 9/00; C07D 233/06
See application file for complete search history.

(56) References Cited

U.S. PATENT DOCUMENTS 5,133,974 A * 7/1992 Paradissis ............ A61K 9/5078
424/475

FOREIGN PATENT DOCUMENTS

| JP | 2010-132561 A | 6/2010 |
| KR | 10-2008-0017489 A | 2/2008 |
| KR | 10-2009-0087494 A | 8/2009 |

OTHER PUBLICATIONS

Hamada M, Ikeda S, Ohshima K, Nakamura M, Kubota N, Ogimoto A, Shigematsu Y. Impact of chronic use of cibenzoline on left ventricular pressure gradient and left ventricular remodeling in patients with hypertrophic obstructive cardiomyopathy. J Cardiol. 2016;67(3):279-86. doi:10.1016/j.jjcc.2015.05.014 (Year: 2016).*
Takehana, Shunji; Sugiyama, Atsushi; Hashimoto, Keitaro, Cardiovascular Effects of Optical Isomers of Cibenzoline, Assessed in the Canine Isolated, Blood-Perfused Papillary Muscle and Sinoatrial Node Preparations Journal of Cardiovascular Pharmacology 34(5):p. 660-665, 1999, (Year: 1999).*
Katsuya Kajimoto, Taku Imai, Yuichiro Minami, Hiroshi Kasanuki Comparison of Acute Reduction in Left Ventricular Outflow Tract Pressure Gradient in Obstructive Hypertrophic Cardiomyopathy by Disopyramide Versus Pilsicainide Versus Cibenzoline; Am J Cardiol 2010;106:1307-1312 (Year: 2010).*
Kevin F. Browne, Eric N. Prystowsky, Douglas P. Zipes, Donald A. Chilson, James J. Heger, Clinical efficacy and electrophysiologic effects of cibenzoline therapy in patients with ventricular arrhythmias, Journal of the American College of Cardiology, vol. 3, No. 3, 1984, pp. 857-864 (Year: 1984).*
Oxford Dictionary of Biochemistry and Molecular Biology: Oxford University Press (2006). Retrieved Mar. 1, 2024, from https://www.oxfordreference.com/view/10.1093/acref/9780198529170.001.0001/acref-9780198529170-e-18905 (Year: 2006).*
Nguyen LA, He H, Pham-Huy C. Chiral drugs: an overview. Int J Biomed Sci. Jun. 2006;2(2):85-100. PMID: 23674971; Pmcid: PMC3614593. (Year: 2006).*
International Search Report from corresponding PCT Application No. PCT/KR2019/014726, dated Feb. 25, 2020.
Hamada, M., et al.; "Antiarrhythmic Drug, Cibenzoline, can Directly Improve the Left Ventricle Diastolic Function in Patients With Hypertrophic Cardiomyopathy", Jpn. Circ. J., vol. 65, pp. 531-538, 2001.
Takehana, S., et al.; "Cardivascular Effects of Optical Isomers of Cibenzoline, Assessed in the Canine Isolated, Blood-Perfused Papillary Muscle and Sinoatrial Node Preparations", Journal of Cardiovascular Pharmacology, vol. 34, pp. 660-665, Nov. 1999.

* cited by examiner

Primary Examiner — Brenda L Coleman
(74) Attorney, Agent, or Firm — Harness, Dickey & Pierce, P.L.C.

(57) ABSTRACT

The present invention relates to a pharmaceutical composition comprising cibenzoline, especially, S(-)-cibenzoline or a pharmaceutically acceptable salt thereof as an active ingredient for treatment of hypertrophic cardiomyopathy, and a method for treatment of hypertrophic cardiomyopathy by using same. The treatment composition and method according to the present invention is used to treat a patient suffering from hypertrophic cardiomyopathy. In addition, the composition and method according to the present invention has excellent efficacy and safety, compared to conventional off-label standard of care (SOC).

11 Claims, 1 Drawing Sheet

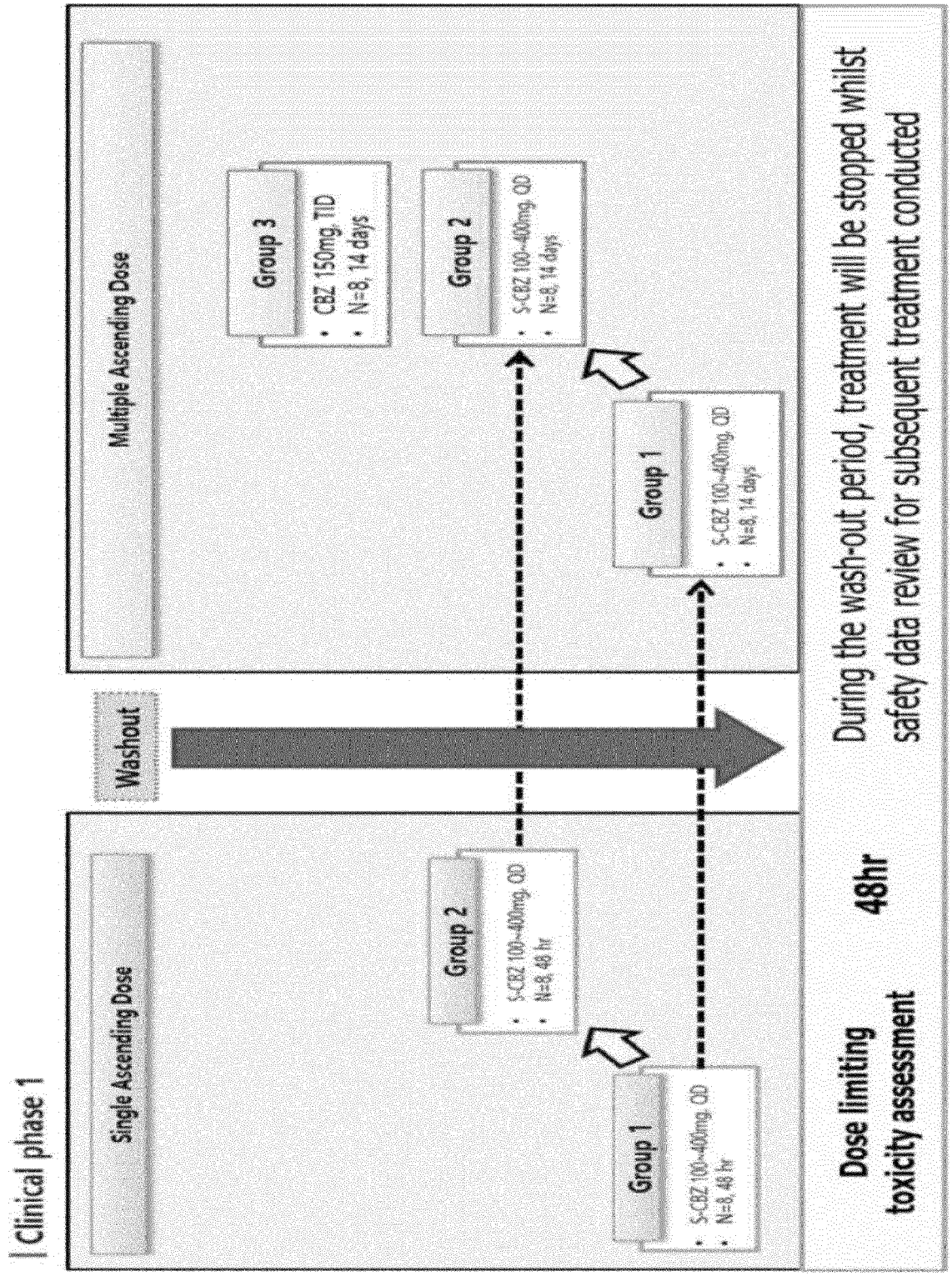

PHARMACEUTICAL COMPOSITION FOR USE IN TREATMENT OF HYPERTROPHIC CARDIOMYOPATHY

CROSS-REFERENCE TO RELATED APPLICATIONS

This application is a national phase application of PCT Application No. PCT/KR2019/014726, filed on 1 Nov. 2019, which claims the benefit and priority to Korean Patent Application No. 10-2018-0133958, filed on 2 Nov. 2018. The entire disclosures of the applications identified in this paragraph are incorporated herein by references.

TECHNICAL FIELD

The present disclosure relates to a pharmaceutical composition for treatment of hypertrophic cardiomyopathy, comprising cibenzoline as an active ingredient, and a method for treatment of hypertrophic cardiomyopathy using same.

BACKGROUND ART

Hypertrophic cardiomyopathy (HCM) is a known disease when septal hypertrophy was observed during autopsy of patients who died suddenly and died after surgery for aortic valve stenosis in the mid-20th century. HCM was initially considered to be a very rare disease, but was currently found to be the most common disease that is highly frequent as 1 of 500 births and causes sudden death especially at a young age, and to have autosomal dominant inheritance.

Currently, there is no drug approved for a treatment method that may be used for hypertrophic cardiomyopathy, but the use of beta blockers, calcium channel blockers, and disopyramide is known in the treatment guidelines. However, the existing off-label standard of care (SOC) only alleviates symptoms of hypertrophic cardiomyopathy and is known to have no effect on fundamental treatments such as suppression of disease progression. If drugs are effective in areas related to symptom control, and prevent or block progression to overt heart failure are present, they are expected to be of great help to affected patients.

According to a thesis of Dr. Hamada who has conducted clinical studies in Japan for decades in treating patients with hypertrophic cardiomyopathy (J Cardiol. 2016 March; 67(3): 279-86), in the case of cibenzoline, class Ia antiarrhythmic drugs of the same class as disopyramide, clinical evidence suggesting that there are fewer side effects than disopyramide and may be effective has been presented. However, there was no control group and were no clinical studies related to actual treatment cases. Therefore, the above study alone may not determine the use and regimen of cibenzoline for hypertrophic cardiomyopathy, and efficacy and safety need to be proven through clinical trials.

It is also known that enantiomers may exhibit differential selectivity for target enzymes in heart and liver tissues in the field of pharmacology. Although the cibenzoline is a drug that exists as two enantiomers, S(−)-cibenzoline and R(+)-cibenzoline, there have been no substantial pharmacological studies on each enantiomer. When a single enantiomer that is pharmacologically effective is found, the dose of the drug administered with a racemic mixture may be reduced through this, and side effects caused by the enantiomer having no effect may be lessened.

The present applicant intended to demonstrate excellent efficacy and stability compared to existing off-label treatment methods when administering cibenzoline to patients with hypertrophic cardiomyopathy, and to define an enantiomer that exhibits pharmacological effect in the two enantiomers of cibenzoline.

SUMMARY

Technical Problem

An object of the present disclosure is to provide a pharmaceutical composition comprising cibenzoline or a pharmaceutically acceptable salt thereof for treatment of hypertrophic cardiomyopathy.

Another object of the present disclosure is to provide a method for treating hypertrophic cardiomyopathy comprising: administering to patients with hypertrophic cardiomyopathy a pharmaceutical composition comprising cibenzoline or a pharmaceutically acceptable salt thereof.

Another object of the present disclosure is to provide a kit comprising a pharmaceutical composition comprising cibenzoline or a pharmaceutically acceptable salt thereof, and instructions to administer the pharmaceutical composition to a subject in order to treat hypertrophic cardiomyopathy.

Technical Solution

The present disclosure provides a pharmaceutical composition for treatment of hypertrophic cardiomyopathy, comprising cibenzoline or a pharmaceutically acceptable salt thereof.

In one embodiment of the present disclosure, the pharmaceutically acceptable salt may be selected from the group consisting of hydrochloride, sulfate, nitrate, phosphate, acetate, trifluoroacetate, benzenesulfonate, succinate, tartaric acid salt, maleate and citrate.

In one embodiment of the present disclosure, the cibenzoline may be a pharmaceutical composition for treatment of hypertrophic cardiomyopathy, comprising S(−)-cibenzoline or a pharmaceutically acceptable salt thereof.

In one embodiment of the present disclosure, the pharmaceutical composition may comprise 200 mg, 300 mg or 400 mg of S(−)-cibenzoline or a pharmaceutically acceptable salt thereof.

In one embodiment of the present disclosure, the pharmaceutical composition may be administered one to three times a day. More specifically, the pharmaceutical composition may be administered once a day or twice a day.

In one embodiment of the present disclosure, the hypertrophic cardiomyopathy may be hypertrophic obstructive cardiomyopathy (HOCM) or hypertrophic non-obstructive cardiomyopathy (HNCM). More specifically, the hypertrophic cardiomyopathy may be hypertrophic obstructive cardiomyopathy (HOCM).

In one embodiment of the present disclosure, the hypertrophic cardiomyopathy may be hypertrophic obstructive cardiomyopathy (HOCM) having one or more of the following characteristics.

a) 15 mm or more of the peak left ventricle thickness (13 mm or more if there is family history);
b) pressure gradient of the resting left ventricular outflow tract (LVOT) being 30 mmHg or more, or 50 mmHg or more after provocation (including stimuli such as Valsalva, standing, or post-exercise, etc.); or
c) 55% or more of left ventricular ejection fraction (LVEF)

In one embodiment of the present disclosure, the pharmaceutical composition may improve a left ventricular pressure gradient (LVPG) value. More specifically, the improvement may be at least 1%, 5%, or 10% or more of change (or decrease) compared to the initial measured value.

In one embodiment of the present disclosure, the pharmaceutical composition may improve a peak volume $O_2$ (PVO$_2$) value.

In one embodiment of the present disclosure, the pharmaceutical composition may improve symptoms classified into the stage of New York Heart Association (NYHA) class.

In one embodiment of the present disclosure, the pharmaceutical composition may be administered in combination with a therapeutic agent for heart disease.

In one embodiment of the present disclosure, the therapeutic agent for heart disease may be selected from the group consisting of beta blockers, calcium channel blockers, and antiarrhythmic drugs.

In addition, the present disclosure provides a method for treating hypertrophic cardiomyopathy comprising administering to patients with hypertrophic cardiomyopathy a pharmaceutical composition comprising cibenzoline or a pharmaceutically acceptable salt thereof.

In one embodiment of the present disclosure, the pharmaceutical composition comprising S(−)-cibenzoline or a pharmaceutically acceptable salt thereof may be administered to patients with hypertrophic cardiomyopathy in a dose of 200 mg, 300 mg, or 400 mg a day.

In one embodiment of the present disclosure, the pharmaceutical composition may be administered to patients with hypertrophic cardiomyopathy one to three times a day. More specifically, the pharmaceutical composition may be administered once a day or twice a day.

In one embodiment of the present disclosure, a patient with hypertrophic cardiomyopathy may be a patient with hypertrophic obstructive cardiomyopathy (HOCM) or hypertrophic non-obstructive cardiomyopathy (HNCM).

In one embodiment of the present disclosure, the treatment method may improve a left ventricular pressure gradient (LVPG) value. More specifically, the improvement may be at least 1%, 5%, or 10% or more of change (or decrease) compared to the initial measured value.

In one embodiment of the present disclosure, the treatment method may improve the peak volume $O_2$ (PVO$_2$) value at early time.

In one embodiment of the present disclosure, the treatment method may improve symptoms classified into the stage of New York Heart Association (NYHA) class.

In one embodiment of the present disclosure, the treatment method may administer a therapeutic agent for heart disease in combination to patients.

In one embodiment of the present disclosure, the therapeutic agent for heart disease may be selected from the group consisting of beta blockers, calcium channel blockers, and antiarrhythmic drugs, but is not limited thereto.

In addition, the present disclosure provides a kit comprising a pharmaceutical composition comprising cibenzoline or a pharmaceutically acceptable salt thereof; and instructions to administer the pharmaceutical composition to patients with hypertrophic cardiomyopathy.

Advantageous Effects

The composition and method for treatment according to the present disclosure treat a patient with hypertrophic cardiomyopathy. In addition, the composition and method according to the present disclosure have excellent efficacy and safety compared to existing off-label treatment methods.

BRIEF DESCRIPTION OF THE DRAWINGS

FIG. 1 is a clinical design for evaluating the stability of cibenzoline.

DETAILED DESCRIPTION

In order to more easily understand the present disclosure, the terms used in the present disclosure are defined below.
Cibenzoline or a Pharmaceutically Acceptable Salt Thereof

[Formula 1]

Formula (III)

Cibenzoline(Cifenline; 2-(2,2-diphenylcyclopropyl)-4,5-dihydro-1H-imidazole; 53267-01-9(CAS number)) is a compound having a structure of formula 1 above and a drug used as antiarrhythmic drugs which is Group 1 sodium channel blocker. In addition, the effects of calcium channel inhibitors and potassium channel inhibitors are also known.

Cibenzoline according to the present disclosure may include not only cibenzoline free salts, but also chlorides thereof, and cibenzoline may be all hydrates and solvates as well as pharmaceutically acceptable salts. In one embodiment, the hydrate or solvate may be a crystallized or recrystallized solvate (especially, a hydrate) after dissolving the cibenzoline in a water-miscible solvent such as methanol, ethanol, acetone, and 1,4-dioxane, and then adding a free acid or a free base. A stoichiometric solvate including hydrates may also be included in addition to various amounts of water-containing compounds that may be prepared by a method such as lyophilization.

The chloride of cibenzoline includes both inorganic and organic acid salts, for example, hydrochloride, sulfate, nitrate, phosphate, acetate, trifluoroacetate, benzenesulfonate, succinate, tartrate, maleate, citrate and the like, but are not limited thereto.

The cibenzoline exists as two enantiomers, S(−)-cibenzoline and R(+)-cibenzoline, and currently commercially available cibenzoline is a composition (a 50:50 mixture of a racemic mixture: an enantiomer) wherein S(−)-cibenzoline and R(+)-cibenzoline are mixed in 1:1. In the present disclosure, S(−)-cibenzoline and a pharmaceutically acceptable salt thereof are more preferred.

The cibenzoline may be formulated for administration to patients, and one or more physiologically acceptable carriers or excipients are included. It means that the carrier is compatible with other components of the formulation and is not harmful to the recipient, and the drug may be formulated for oral, intravenous or rectal administration, etc. Examples of formulation may be formulated in conventional forms such as tablets, capsules, and syrup, but are not limited thereto.

Hypertrophic Cardiomyopathy (HCM)

Hypertrophic cardiomyopathy includes a group of highly expressed, monogenic, autosomal dominant myocardial diseases. It is caused by one or more of 1,000 or more known point mutations in any one of the structural protein genes that contribute to the eradication of the functional unit of the myocardium. HCM was initially considered to be a very rare disease, but was currently found to be the most common disease that is highly frequent as 1 of 500 births and causes sudden death especially at a young age, and to have autosomal dominant inheritance. In most young adults, electrocardiogram and echocardiography are performed for health checkups, and follow-up observations are often performed after accidental discovery.

Hemodynamic or symptomatic hypertrophic cardiomyopathy may be divided into obstructive and non-obstructive types. The obstructive type may be divided into sub-valve obstruction and ventricular central occlusion, and the delayed obstructive type refers to a case where there is no pressure gradient at rest, but the gradient occurs in not less than 30 mmHg during provocation.

Clinical symptoms for patients with hypertrophic cardiomyopathy are motor dyspnea, including systemic arterial thromboembolic disease including stroke, acute pulmonary edema, atrial fibrillation, intolerance of volemia or hypervolemia, and fainting. Recently, sudden cardiac death (SCD) has also been identified as a major symptom of hypertrophic cardiomyopathy.

Subject

Subjects include all human or non-human animals. The term "non-human animal" includes, but is not limited to, vertebrates such as non-human primates, sheep, dogs, cats, rabbits and ferrets, rodents, birds, amphibians, and reptiles. In one embodiment, the subject is a mammal, a human, a non-human primate, a sheep, a dog, a cat, a rabbit, a ferret or a rodent. In the present disclosure, the terms "subject", "patient" and "individual" are used interchangeably.

Administration

It refers to the administration of a substance (e.g., cibenzoline or a pharmaceutically acceptable salt thereof) to achieve a therapeutic purpose (e.g., treatment of hypertrophic cardiomyopathy). The administration may be carried out orally or parenterally, and in the case of parenteral administration, it may be intravenous injection, subcutaneous injection, intramuscular injection, intraperitoneal injection, endothelial administration, topical administration, intranasal administration, intrapulmonary administration, and rectal administration, etc. The administration includes all methods of delivering a drug to a subject in order to achieve a therapeutic purpose.

Dosage

A suitable dosage of the pharmaceutical composition of the present disclosure may be selected by various ways depending on factors such as a formulation method, a mode of administration, age, weight, sex, a pathological condition, food, administration time, route of administration, excretion rate and response sensitivity of the patient.

In one embodiment of the present disclosure, a daily dosage of the pharmaceutical composition of the present disclosure may be 200 mg, 300 mg or 400 mg.

Administration Frequency

A suitable administration frequency of the pharmaceutical composition of the present disclosure may be selected by various ways depending on factors such as a formulation method, a mode of administration, age, weight, sex, a pathological condition, food, administration time, route of administration, excretion rate and response sensitivity of the patient.

In one embodiment of the present disclosure, the administration frequency per day of the pharmaceutical composition of the present disclosure may be one to five times a day, three times a day, twice a day, or once a day, more specifically, once a day or twice a day.

Kit

A kit refers to a packaged product containing components for administering the cibenzoline of the present disclosure or a pharmaceutically acceptable salt thereof for treatment of hypertrophic cardiomyopathy. The kit includes a container or box that holds the components of the kit. The box or container is accompanied by a protocol or label approved by the Food and Drug Administration. The box or container holds the components of the present disclosure, contained within a plastic, polyethylene, polypropylene, ethylene or propylene container. The container may be a tube or bottle with a lid. The kit also includes instructions for administering the cibenzoline of the present disclosure or a pharmaceutically acceptable salt thereof.

Left Ventricular Pressure Gradient (LVPG)

The left ventricular pressure gradient refers to the difference between the left ventricular systolic blood pressure and the left ventricular diastolic blood pressure when the left ventricle pressure, which is the blood pressure in the left ventricle of the heart, is measured.

When the left ventricular pressure gradient decreases, it is known that the risk of heart failure, etc., due to hypertrophic cardiomyopathy decreases, and the left ventricular pressure gradient may be used as a factor for evaluating treatment methods such as exercise, drugs, or devices in relation to heart disease.

Peak Volume $O_2$ ($PVO_2$)

Peak oxygen consumption may be clinically quantified by measuring oxygen uptake ($V_{O_2}$), carbon dioxide production ($V_{CO_2}$), and minute ventilation (total amount of gas release from lugs for 1 minute). The peak oxygen consumption is determined by measuring the concentrations of each $O_2$ and $CO_2$ measured in the inhaled and exhaled air during exercise with a gas analyzer.

The peak oxygen consumption is a standard indicator for evaluating cardiovascular health and a strong prognostic indicator for chronic heart failure. Although the peak oxygen consumption is said to be proportional to body mass, it changes depending on a variety of factors, including drugs, devices, exercise, and weight changes. The peak oxygen consumption may be used as a factor in evaluating treatment method, such as exercise, drugs or devices in relation to heart disease.

New York Heart Association (NYHA) Classification

The severity of heart failure (loss of heart function) is classified into four stages according to subjective symptoms based on the classification of the New York Heart Association. When there was no measurable factor for heart donation in 1902, it was established to differentiate patients among doctors, but it is still used as an important determinant in heart failure.

[The Classification of Four Stages by NYHA]
  Group 1 (A): Patients with no restrictive activity. There are no symptoms from daily activities.
  Group 2 (B): Patients with mild restrictive activity. There are no symptoms with stable and moderate movements.
  Group 3 (C): Patients with significant restrictive activity. There are no symptoms only at rest.

Group 4 (D): Patients who require complete stability and should live in a bed or chair. Even a slight movement leads to unpleasant symptoms.

Electrocardiogram (ECG)

Electrocardiogram refers to a picture showing the recording of the myocardial activity current by inducing the active current generated in the myocardium according to the heartbeat to two suitable places on the body surface and recording it with an ammeter. In general, a 12-point guided electrocardiogram system is used, through which the heart rate, the electrical axis of the heart, and the degree of rotation may be evaluated, and the presence or absence of a conduction abnormality in the ventricle may be also noted.

The waveform of the electrocardiogram signal displays the electric current and potential difference caused by the contraction of the heart as a curve. In general, P wave, Q wave, R wave, S wave, and T wave occur continuously within one period of the electrocardiogram signal. The P wave represents the contraction of the atrium, a series of Q wave, R wave and S wave represent the contraction of the ventricle, and the T wave is a characteristic that appears when the ventricle is relaxed.

QRS (QRS-complex) appears as a combination of Q, R, and S waves related to ventricular contraction, and QRS wave indicate that excitation is transmitted to the ventricles and the heart contracts.

QTc is defined as the correction of the QT interval, which is the interval between the Q wave and the T wave, with the heart rate. Among the methods of calculating QTc, it is defined as QTcF by using the correction formula of a Fridericia method ($QTcF=QT/RR^{0.33}$).

Improvement

The improvement of the present disclosure means improving the clinical or pathological condition of the patient than before the drug administration.

In one embodiment of the present disclosure, improving the LVPG value of the pharmaceutical composition may mean a change (or decrease) of at least 1%, 5%, or 10% or more compared to the initial measured value. In addition, in the case of the left ventricular pressure gradient (LVPG) value, the value may converge to zero.

In one embodiment of the present disclosure, the meaning of improving the peak oxygen consumption ($PVO_2$) value may be an increase of at least 1%, 5%, or 10% or more compared to the initial measured value.

In one embodiment of the present disclosure, the pharmaceutical composition improves symptoms classified into New York Heart Association (NYHA) class stages means decreasing the class of symptoms classified as intra or inter change. For example, it means that the patients classified into severity of 3rd stage of the New York Heart Association classification (NYHA class) are classified into mild symptom of $3^{rd}$ stage of New York Heart Association (NYHA) class, and $2^{nd}$ stage of New York Heart Association (NYHA) class, but is not limited thereto.

Combination Administration

Cibenzoline of the present disclosure or a pharmaceutically acceptable salt thereof and other therapeutic agents for heart disease may be administered. Administration is carried out concurrently with, before or after administration of cibenzoline or a pharmaceutically acceptable salt thereof.

In one embodiment of the present disclosure, the therapeutic agent for heart disease, administered in combination may be beta blockers, calcium channel blockers, and antiarrhythmic drugs, but is not limited thereto.

In one embodiment of the present disclosure, examples of the drugs for treating heart disease, administered in combination include, but are not limited to, athenolol, metoprolol, bisoprolol, propranolol, diltiazem, verapamil, amlodipine, disopyramide, etc.

Hereinafter, the present disclosure will be described in detail by Examples. The following Examples are only illustrative of the present disclosure, and do not limit the scope of present disclosure in any way.

Example 1. Clinical Stability Evaluation of Cibenzoline on Healthy Subjects (Once, Single Administration)

This study is a clinical study to evaluate safety and tolerability by administering 200 mg or 300 mg of S(−)-cibenzoline orally once a day or 150 mg of cibenzoline of racemic mixture orally three times a day to healthy subjects for 3 weeks. More specifically, the clinical trial was conducted by administering as follows.

Cohort 1: S(−)-cibenzoline 200 mg once a day by one oral administration

Cohort 2: S(−)-cibenzoline 300 mg once a day by one oral administration

Cohort 3: Racemic mixture, cibenzoline 150 mg 3 times a day by the oral administration Randomized, double-blind, placebo-controlled, sequential, ascending, single dosing studies were conducted to evaluate safety, tolerability, pharmacokinetics and pharmacodynamics of cibenzoline.

In this study, a total of 24 subjects were randomly assigned 1:1:1 to three cohorts and proceeded in a total of four stages: screening, treatment period 1, withdrawal period, and treatment period 2. The ratio between the dosed group and the non-dosed group (placebo) is assigned as 6:2.

The main endpoints are safety, tolerability and side effects, and the clinical test items are corrected QT interval (calculated by Fridericia formula) [QTc(F)]), QT interval, and QRS interval, PR interval, and 12-electrode electrocardiogram including ventricular rate, vital signs (blood pressure, pulse, body temperature, respiration rate), hypersensitivity reaction (determined by electrocardiogram recording and vital signs), clinical inspection evaluation (hematology, blood chemistry, urinalysis, etc.), adverse reactions (including serious adverse reactions).

In addition, in order to analyze the blood pharmacokinetics of the increase in the dose of cibenzoline in healthy subjects, the area under the concentration-time curve (AUC), the highest drug concentration in the blood ($C_{max}$), and the time to reach the highest blood concentration ($t_{max}$), and the half-life of the highest blood concentration ($t_{1/2}$) are measured.

In addition, for the pharmacodynamic analysis of cibenzoline in healthy subjects, the left ventricular ejection fraction, the left ventricular systolic and diastolic dimensions, and the velocity time integral were measured.

Through the above clinical trials, it was confirmed that cohorts 1 and 2 did not cause significant side effects when compared to cohort 3, which is used as a conventional drug therapy. Through this, the safety and tolerability for dose therapy of S(−)-cibenzoline of 200 mg and 300 mg once a day were confirmed.

Additionally, as shown in Table 1 below, the effects of QcTF and QRS prolongation were confirmed as a result of inspecting electrocardiography patients in cohorts 1 and 2.

TABLE 1

|  | Day 1 (before administration) | Day 1 (1.5 h after administration) | Day 1 (3 h after administration) | Day 1 (8 h after administration) |
|---|---|---|---|---|
| Cohort 1 |  |  |  |  |
| QTcF (ms) | 406 | 412 | 426 | 408 |
| QRS (ms) | 92 | 102 | 107 | 99 |
| Cohort 2 |  |  |  |  |
| QTcF (ms) | 411 | 419 | 429 | 415 |
| QRS (ms) | 101 | 107 | 116 | 107 |

Example 2. Clinical Stability Evaluation of Cibenzoline on Healthy Subjects (Single Repeated Administration)

This study is a clinical trial to evaluate safety and tolerability by conducting clinical trials in patient groups of the following cohorts 4 to 6 in healthy subjects.

Cohort 4: S(−)-cibenzoline 200 mg once a day/oral administration for a total of 5 days Cohort 5: S(−)-cibenzoline 300 mg once a day/oral administration for a total of 14 days Cohort 6: Racemic mixture, cibenzoline 150 mg 3 times a day/oral administration for a total of 14 days Randomized, double-blind, placebo-controlled, sequential, ascending, single dose, and repeated dosing studies were conducted to evaluate safety, tolerability, pharmacokinetics and pharmacodynamics of cibenzoline.

In this study, a total of 24 subjects were randomly assigned 1:1:1 to three cohorts and proceeded in a total of four stages: screening, treatment period 1, withdrawal period, and treatment period 2. The ratio between the dosed group and the non-dosed group (placebo) is assigned as 6:2.

The main endpoints are safety, tolerability and side effects, and the clinical test items are corrected QT interval (calculated by Fridericia formula) [QTc(F)]), QT interval, and QRS interval, PR interval, and 12-electrode electrocardiogram including ventricular rate, vital signs (blood pressure, pulse, body temperature, respiration rate), hypersensitivity reaction (determined by electrocardiogram recording and vital signs), clinical inspection evaluation (hematology, blood chemistry, urinalysis, etc.), adverse reactions (including serious adverse reactions).

In addition, in order to analyze the blood pharmacokinetics of the increase in the dose of cibenzoline in healthy subjects, the area under the concentration-time curve (AUC), the highest drug concentration in the blood ($C_{max}$), and the time to reach the highest blood concentration ($t_{max}$), and the half-life of the highest blood concentration ($t_{1/2}$) were measured.

In addition, for the pharmacodynamic analysis of cibenzoline in healthy subjects, the left ventricular ejection fraction, the left ventricular systolic and diastolic dimensions, and the velocity time integral were measured.

Through the clinical trials above, it was confirmed that cohorts 4 and 5 did not cause significant side effects for multiple administration when compared to cohort 6, which is used as a conventional drug therapy. Through this, the safety and tolerability for dose therapy of S(−)-cibenzoline of 200 mg and 300 mg once a day were confirmed.

Additionally, as same as the single administration of Example 1, the effects of QcTF and QRS prolongation were confirmed as a result of inspecting electrocardiography of patients in cohorts 4 and 5.

Example 3. Clinical Stability Evaluation of Cibenzoline in Patients with Hypertrophic Cardiomyopathy This study is a clinical trial to evaluate the efficacy and safety of cibenzoline by conducting clinical trials in patients with symptomatic hypertrophic obstructive cardiomyopathy (Symptomatic Obstructive HCM, HOCM) in the following cohort 1 to 3 patient groups.

Cohort 1: S(−)-cibenzoline 200 mg once a day/oral administration for a total of 5 days Cohort 2: S(−)-cibenzoline 300 mg once a day/oral administration for a total of 5 days Cohort 3: S(−)-cibenzoline 200 mg twice a day/oral administration for a total of 5 days In this study, a total of 24 subjects were randomly assigned 1:1:1 to three cohorts and proceeded in a total of four stages: screening, treatment period 1, withdrawal period, and treatment period 2. The ratio between the dosed group and the non-dosed group (placebo) is assigned as 6:2.

The evaluation of patients as subjects is conducted based on the following criteria.

A patient with the maximum left ventricle thickness of 15 mm or more (a patient with the thickness of 13 mm or more, if there is a family history)

A patient with pressure gradient of the resting left ventricular outflow tract (LVOT) being 30 mmHg or more, or 50 mmHg or more after provocation (including stimuli such as Valsalva, standing, or post-exercise, etc.)

Patient with 55% or more of left ventricular ejection fraction (LVEF)

This study proceeds in the screening stage and the treatment stage. Open label, non-randomized, active-controlled, and multicenter studies are performed.

The main endpoints are safety, tolerability and side effects, and the clinical test items are corrected QT interval (calculated by Fridericia formula) [QTc(F)]), QT interval, and QRS interval, PR interval, and 12-electrode electrocardiogram including ventricular rate, vital signs (blood pressure, pulse, body temperature, respiration rate), hypersensitivity reaction (determined by electrocardiogram recording and vital signs), clinical inspection evaluation (hematology, blood chemistry, urinalysis, etc.), adverse reactions (including serious adverse reactions).

Secondary endpoints are pharmacokinetics including $C_{max}$, left ventricular pressure gradient (LVPG) and left ventricular ejection fraction (LVEF) through transthoracic echocardiography (TTE), and additionally, B-natriuretic peptide (BNP) and Troponin levels in blood.

What is claimed is:

1. A method for treating hypertrophic cardiomyopathy, comprising:
    administering to a subject in need thereof a composition comprising a therapeutically effective amount of S(−)-cibenzoline or a pharmaceutically acceptable salt thereof.

2. The method of claim 1, wherein the pharmaceutically acceptable salt is selected from the group consisting of hydrochloride, sulfate, nitrate, phosphate, acetate, trifluoroacetate, benzenesulfonate, succinate, tartrate, maleate, and citrate.

3. The method of claim 1, wherein the composition comprises 200 mg, 300 mg or 400 mg of S(−)-cibenzoline or a pharmaceutically acceptable salt thereof.

4. The method of claim 1, wherein the composition is administered one to three times a day.

5. The method of claim 4, wherein the composition is administered once a day or twice a day.

6. The method of claim 1, wherein the hypertrophic cardiomyopathy is hypertrophic obstructive cardiomyopathy (HOCM) or hypertrophic non-obstructive cardiomyopathy (HNCM).

7. The method of claim 1, wherein the hypertrophic cardiomyopathy is hypertrophic obstructive cardiomyopathy (HOCM).

8. The method of claim 1, wherein the hypertrophic cardiomyopathy is hypertrophic obstructive cardiomyopathy (HOCM) having one or more of the following features:
   a) 15 mm or more of the peak left ventricle thickness or 13 mm or more if there is family history; or
   b) pressure gradient of the resting left ventricular outflow tract (LVOT) being 30 mmHg or more, or 50 mmHg or more after provocation, wherein provocation includes stimuli which is Valsalva, standing, or post-exercise.

9. The method of claim 1, wherein the composition improves a left ventricular pressure gradient (LVPG) value.

10. The method of claim 9, wherein the improvement is at least 1%, 5%, or 10% or more decrease compared to the initial measured value.

11. The method of claim 1, wherein the composition is administered in combination with a therapeutic agent for a heart disease,
   wherein the therapeutic agent for a heart disease is selected from the group consisting of athenolol, metoprolol, bisoprolol, propranolol, diltiazem, verapamil, amlodipine, and disopyramide.

* * * * *